US011627857B2

(12) United States Patent
Xing et al.

(10) Patent No.: US 11,627,857 B2
(45) Date of Patent: Apr. 18, 2023

(54) METHOD AND APPARATUS FOR REMOVING MITES

(71) Applicant: BEIJING XIAOMI MOBILE SOFTWARE CO., LTD., Beijing (CN)

(72) Inventors: Zheng Xing, Beijing (CN); Yingchun Xie, Beijing (CN)

(73) Assignee: BEIJING XIAOMI MOBILE SOFTWARE CO., LTD., Beijing (CN)

( * ) Notice: Subject to any disclaimer, the term of this patent is extended or adjusted under 35 U.S.C. 154(b) by 550 days.

(21) Appl. No.: 16/744,045

(22) Filed: Jan. 15, 2020

(65) Prior Publication Data

US 2021/0127936 A1 May 6, 2021

(30) Foreign Application Priority Data

Oct. 31, 2019 (CN) .......................... 201911050740.5

(51) Int. Cl.
*A47L 11/40* (2006.01)
*A61L 2/10* (2006.01)
(Continued)

(52) U.S. Cl.
CPC ......... *A47L 11/4044* (2013.01); *A47L 11/405* (2013.01); *A61L 2/10* (2013.01);
(Continued)

(58) Field of Classification Search
CPC ............... A47L 11/4044; A47L 11/405; A47L 2201/04; A47L 2201/06; A47L 2201/00; A47L 25/00; A47L 7/0085; A47L 7/009; A47L 9/00; A47L 9/2805; A47L 9/2836; A47L 9/2852; A61L 2/10; G05D 1/0212; G05D 1/0227; G05D 1/0223; G05D 1/0214; G05D 1/021; G05D 2201/0215;
(Continued)

(56) References Cited

U.S. PATENT DOCUMENTS 9,526,387 B1 * 12/2016 Li ........................... A47L 7/008
2015/0041227 A1 * 2/2015 Jun ..................... B62D 57/032
901/1
(Continued)

FOREIGN PATENT DOCUMENTS

CN 102179812 A * 9/2011
CN 104802871 A * 7/2015
(Continued)

OTHER PUBLICATIONS

First office action of Chinese application No. 201911050740.5 dated Nov. 4, 2020.
(Continued)

*Primary Examiner* — Khoi H Tran
*Assistant Examiner* — Nhi Q Bui
(74) *Attorney, Agent, or Firm* — Syncoda LLC; Feng Ma

(57) ABSTRACT

A method of removing mites includes: acquiring a target path for mite removal and switching from a hibernation state to a crawling state upon receiving a mite removing instruction; in the crawling state, crawling according to the target path and performing mite removal during the crawling process; and after crawling to an end position of the target path, switching from the crawling state to the hibernation state.

19 Claims, 8 Drawing Sheets

Detection component

(51) Int. Cl.
*G05D 1/02* (2020.01)
*G06F 9/4401* (2018.01)

(52) U.S. Cl.
CPC ......... *G05D 1/0212* (2013.01); *G06F 9/4418* (2013.01); *A47L 2201/04* (2013.01); *A47L 2201/06* (2013.01); *G05D 2201/0215* (2013.01)

(58) Field of Classification Search
CPC .... G06F 9/4418; A01M 17/00; B62D 57/032; B62D 57/02; B62D 57/028; B62D 57/024; B62D 5/0463; B25J 9/126
See application file for complete search history.

(56) References Cited

U.S. PATENT DOCUMENTS

| | | | | |
|---|---|---|---|---|
| 2018/0021942 A1* | 1/2018 | Hummel | ............... | G05D 1/0242 700/253 |
| 2019/0246858 A1* | 8/2019 | Karasikov | ................ | B25J 5/007 |
| 2020/0069140 A1* | 3/2020 | Orzechowski | ....... | G05D 1/0022 |
| 2021/0283773 A1* | 9/2021 | Ahn | ...................... | A47L 9/2857 |

FOREIGN PATENT DOCUMENTS

| | | | | | |
|---|---|---|---|---|---|
| CN | 204765401 | U | | 11/2015 | |
| CN | 105476555 | A | | 4/2016 | |
| CN | 106075493 | A | * | 11/2016 | ........... A47L 7/0061 |
| CN | 106075493 | A | | 11/2016 | |
| CN | 107116980 | A | * | 9/2017 | ........... B60F 3/0007 |
| CN | 206548853 | U | | 10/2017 | |
| CN | 207253305 | U | | 4/2018 | |
| CN | 107995279 | A | | 5/2018 | |
| CN | 108583178 | A | * | 9/2018 | ........... B60F 3/0007 |
| CN | 108803600 | A | * | 11/2018 | ........... G05D 1/0212 |
| CN | 108803600 | A | | 11/2018 | |
| CN | 108859637 | A | * | 11/2018 | ........... B60F 3/0007 |
| KR | 20110006422 | U | | 6/2011 | |

OTHER PUBLICATIONS

Extended European search report of counterpart EP application No. 20153155.5 dated Jul. 27, 2020.

* cited by examiner

METHOD AND APPARATUS FOR REMOVING MITES

CROSS-REFERENCE TO RELATED APPLICATION

This application claims priority to Chinese Patent Application No. 201911050740.5, filed on Oct. 31, 2019, the disclosure of which is hereby incorporated by reference in its entirety.

BACKGROUND

Mites are microorganisms that often breed on beds, sofas, carpets, and other places, which can cause discomfort to users upon contact. Therefore, mites need to be removed frequently to ensure users' health.

SUMMARY

Embodiments of the present disclosure relate to a method of removing mites, and a mite remover.

Various embodiments of the present disclosure provide a method of removing mites, which is applicable to a crawling mite remover, and the method including:

acquiring a target path for mite removal and switching from a hibernation state to a crawling state upon receiving a mite removing instruction;

in the crawling state, crawling according to the target path and performing mite removal during the crawling process; and after crawling to an end position of the target path, switching from the crawling state to the hibernation state.

In some embodiments, the method further includes:

determining a current position of the mite remover as an original position upon receiving the mite removing instruction; and in the crawling state, crawling according to the target path and performing mite removal during the crawling process include:

crawling from the original position to a start position of the target path based on the crawling state; and crawling according to the target path from the start position and performing mite removal during the crawling process.

In some other embodiments, after crawling to the end position of the target path, switching from the crawling state to the hibernation state includes:

when crawling to the end position of the target path, continuing crawling to the original position; and switching from the crawling state to the hibernation state upon crawling to the original position.

In some other embodiments, the method further includes:

determining a time when crawling to the start position of the target path as a start time of mite removal;

determining a time when crawling to the end position of the target path as an end time of mite removal; and generating a mite removing log, the mite removing log including the start time of mite removal and the end time of mite removal; or the mite removing log including the start time of mite removal and a mite removing duration, the mite removing duration being determined by the start time of mite removal and the end time of mite removal.

In some other embodiments, the method further includes:

sending the mite removing log to a connected terminal, and displaying the mite removing log by the terminal.

In some other embodiments, acquiring a target path for mite removal and switching from a hibernation state to a crawling state upon receiving a mite removing instruction include:

when receiving the mite removing instruction and determining that no moving object exists within a preset range, acquiring the target path and switching from the hibernation state to the crawling state.

Various embodiments of the present disclosure also provide a mite remover, including a processor, a body, a first motor, and a plurality of legs, the plurality of legs is disposed on a side of the body;

the processor and the first motor are disposed inside the body, the processor is connected to the first motor, and the first motor is connected to the plurality of legs;

the processor sends a movement signal to the first motor; and based on the movement signal, the first motor drives the plurality of legs to perform a telescopic movement to drive the body to move on a surface of an object, and the body performs mite removal on the surface of the object.

In some other embodiments, a dust box is provided at a top of the body, and a dust suction port is provided at a bottom of the body;

a passage is provided inside the body, and a turbine is provided in the passage;

the interior of the dust box, the passage and the dust suction port are in communication; and the turbine rotates to suck dust on the surface of the object into the dust box through the passage from the dust suction port.

In some other embodiments, an ultraviolet lamp is provided at the bottom of the body; and the ultraviolet lamp irradiates the surface of the object, and ultraviolet rays emitted by the ultraviolet lamp perform mite removal.

In some other embodiments, an upper shell is provided on an outer side of the dust box, the body is provided with a bearing and a second motor, and the upper shell is connected to the body through the bearing;

the processor sends a steering signal to the second motor; and based on the steering signal, the second motor drives the bearing to rotate and drive the body to rotate relative to the upper shell and to steer on the surface of the object.

In some other embodiments, the body is provided with a sensor, and the sensor is connected to the processor; and the sensor detects a position of the mite remover relative to the object, and when it is determined that the mite remover is located at an edge of the object, sends the steering signal to the processor In some other embodiments, the mite remover further includes a communication module, the communication module is connected to the processor; and the communication module receives a target path sent by a terminal, and sends the target path to the processor.

In some other embodiments, the body further includes a positioning member, and the positioning member is connected to the processor;

the positioning component detects a current position of the mite remover and sends the current position to the processor; and the processor controls the first motor according to a positional relationship between the position and the target path.

In some other embodiments, each of the plurality of legs includes a connector and a lower shell, the first motor is connected to the connector, and the connector is connected to the lower shell; and the first motor drives the connector to perform a telescopic movement and drive the lower shell to move on the surface of the object, and the body performs mite removal on the surface of the object.

In some other embodiments, an upper shell is provided on an outer side of the dust box, the upper shell is hemispherical, and the lower shells of the plurality of legs are arc-shaped; and the first motor drives the connectors of the plurality of legs to telescope and drive the lower shells of the plurality of legs to fit on the side of the body and contact the upper shell, and the upper shell and the lower shells of the plurality of legs constitute a sphere.

In some other embodiments, the connector includes a first joint and a second joint;

the first motor is connected to the first joint, the first joint is connected to the second joint, and the second joint is connected to the lower shell;

a third motor is provided between the first joint and the second joint;

the processor sends the movement signal to the third motor; and based on the movement signal, the third motor drives the second joint to rotate relative to the first joint.

Various embodiments of the present disclosure also provide a method of removing mites, which is applicable to a mite remover, wherein the mite remover includes a processor, a body, a first motor, and a plurality of legs; the plurality of legs is provided on a side of the body; the processor and the first motor are disposed inside the body, the processor is connected to the first motor, and the first motor is connected to the plurality of legs; and the method includes:

when receiving a mite removing instruction, the processor sends a movement signal to the first motor; and based on the movement signal, the first motor drives the plurality of legs to perform a telescopic movement and drive the body to move on a surface of an object, and the body performs mite removal on the surface of the object.

In some embodiments, a dust box is provided at a top of the body and a dust suction port is provided at a bottom of the body; a passage is provided inside the body, and a turbine is provided in the passage; the interior of the dust box, the passage and the dust suction port are in communication; and the body performing mite removal on the surface of the object includes:

the turbine rotates to suck dust on the surface of the object into the dust box through the passage from the dust suction port.

In some other embodiments, an ultraviolet lamp is disposed at the bottom of the body; and the body performing mite removal on the surface of the object includes:

the ultraviolet lamp irradiates the surface of the object, and ultraviolet rays emitted by the ultraviolet lamp perform mite removal.

In some other embodiments, the mite remover further includes a detection component, the detection component is connected to the processor, and the method further includes:

the processor controls the detection component to detect whether a moving object exists within a preset range of the mite remover; and when the processor receives the mite removing instruction and determines that no moving object exists within the preset range, the processor sends the movement signal to the first motor.

In some other embodiments, an upper shell is provided on an outer side of the dust box, the body is provided with a bearing and a second motor, and the upper shell is connected to the body through the bearing; the body is provided with a sensor, and the sensor is connected to the processor; and the method further includes:

the sensor detects a position of the mite remover relative to the object;

when it is determined that the mite remover is located at an edge of the object, sending the steering signal to the processor;

the processor sends the steering signal to the second motor; and based on the steering signal, the second motor drives the bearing to rotate and drive the body to rotate relative to the upper shell and to steer on the surface of the object.

In some other embodiments, the mite remover further includes a communication module, the communication module is connected to the processor, and the method further includes:

the communication module receives a target path sent by a terminal, and sends the target path to the processor.

In some other embodiments, the body further includes a positioning component, and the positioning component is connected to the processor; and the method further includes:

the positioning component detects a first position of the mite remover and sends the first position to the processor; and the processor controls the first motor according to a positional relationship between the first position and the target path.

It is to be understood that the above general description and the following detailed description are merely exemplary and explanatory, and do not limit the present disclosure.

BRIEF DESCRIPTION OF THE DRAWINGS

The accompanying drawings, which are incorporated in and constitute a part of this disclosure, illustrate embodiments consistent with the present disclosure and, together with the description, serve to explain the principles of the present disclosure.

DETAILED DESCRIPTION

Various embodiments of the present disclosure will be described in further detail with reference to the accompanying drawings, to present the objects, technical solutions, and advantages of various embodiments of the present disclosure more clearly.

A mite remover can include a handle, a suction head, a cleaning cartridge, and a body. The handle, the suction head, and the cleaning cartridge are respectively connected to the body. A passage inside the suction head and a passage inside the body are in communication. The passage inside the body is in communication with the interior of the cleaning cartridge. When using the mite remover, a user holds the handle and moves the handle to move the body, the cleaning cartridge and the suction head, and attach the suction head to the position where mite removal is needed. Suction is generated inside the body to suck the mites and the dust produced by the mites into the passage through the suction head and transmitted to the cleaning cartridge through the passage. The handle may be moved continuously to change the position where mite removal is needed.

When using the above-mentioned mite remover, the user may need to move the handle to complete mite removal, which is inconvenient for the user.

Figure 1:
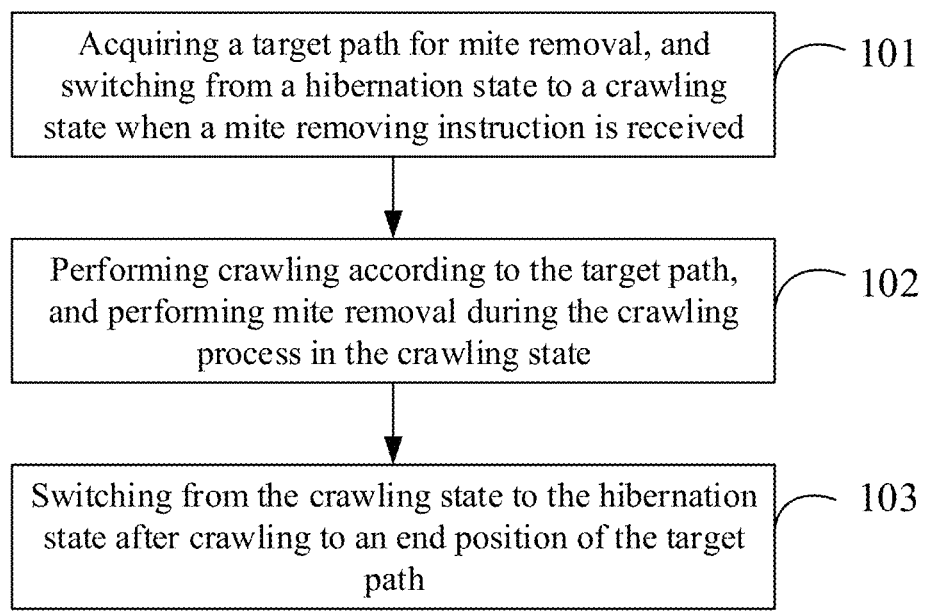
FIG. 1 is a flowchart illustrating a method of removing mites according to some embodiments.

FIG. 1 is a flowchart illustrating a method of removing mites according to some embodiments, which is applicable to a crawling mite remover. As illustrated in FIG. 1, the method comprises the following steps.

In step 101, when a mite removing instruction is received, a target path for mite removal is acquired, and it is switched from a hibernation state to a crawling state.

In step 102, in the crawling state, crawling is performed according to the target path, and mite removal is performed during the crawling process.

In step 103, after crawling to an end position of the target path, it is switched from the crawling state to the hibernation state.

According to the method provided in the embodiment of the present disclosure, when a mite removing instruction is received, a target path for mite removal is acquired, it is switched from a hibernation state to a crawling state, crawling is performed according to the target path, mite removal is performed during the crawling process, and after crawling to an end position of the target path, it is switched from the crawling state to the hibernation state. The method of removing mites according to the embodiment of the present disclosure does not require user operation during the mite removal process, and can automatically complete mite removal, which is convenient for users.

In some embodiments of the present disclosure, the method further comprises:

when receiving the mite removing instruction, determining a current position of the mite remover as an original position; and in the crawling state, crawling according to the target path and performing mite removal during the crawling process comprise:

crawling from the original position to a start position of the target path based on the crawling state; and crawling from the start position according to the target path and performing mite removal during the crawling process.

In some embodiments of the present disclosure, after crawling to the end position of the target path, switching from the crawling state to the hibernation state comprises:

when crawling to the end position of the target path, continuing crawling to the original position; and when crawling to the original position, switching from the crawling state to the hibernation state.

In some embodiments of the present disclosure, the method further comprises:

determining a time when crawling to the start position of the target path as a start time of mite removal;

determining a time when crawling to the end position of the target path as an end time of mite removal; and generating a mite removing log, the mite removing log comprising the start time of mite removal and the end time of mite removal; or the mite removing log comprising the start time of mite removal and a mite removing duration, the mite removing duration being determined by the start time of mite removal and the end time of mite removal.

In some embodiments of the present disclosure, the method further comprises:

sending the mite removing log to a connected terminal, and displaying the mite removing log by the terminal.

In some embodiments of the present disclosure, when receiving a mite removing instruction, acquiring a target path for mite removal and switching from a hibernation state to a crawling state comprises:

when receiving the mite removing instruction and determining that no moving object exists within a preset range, acquiring the target path and switching from the hibernation state to the crawling state.

Figure 2:
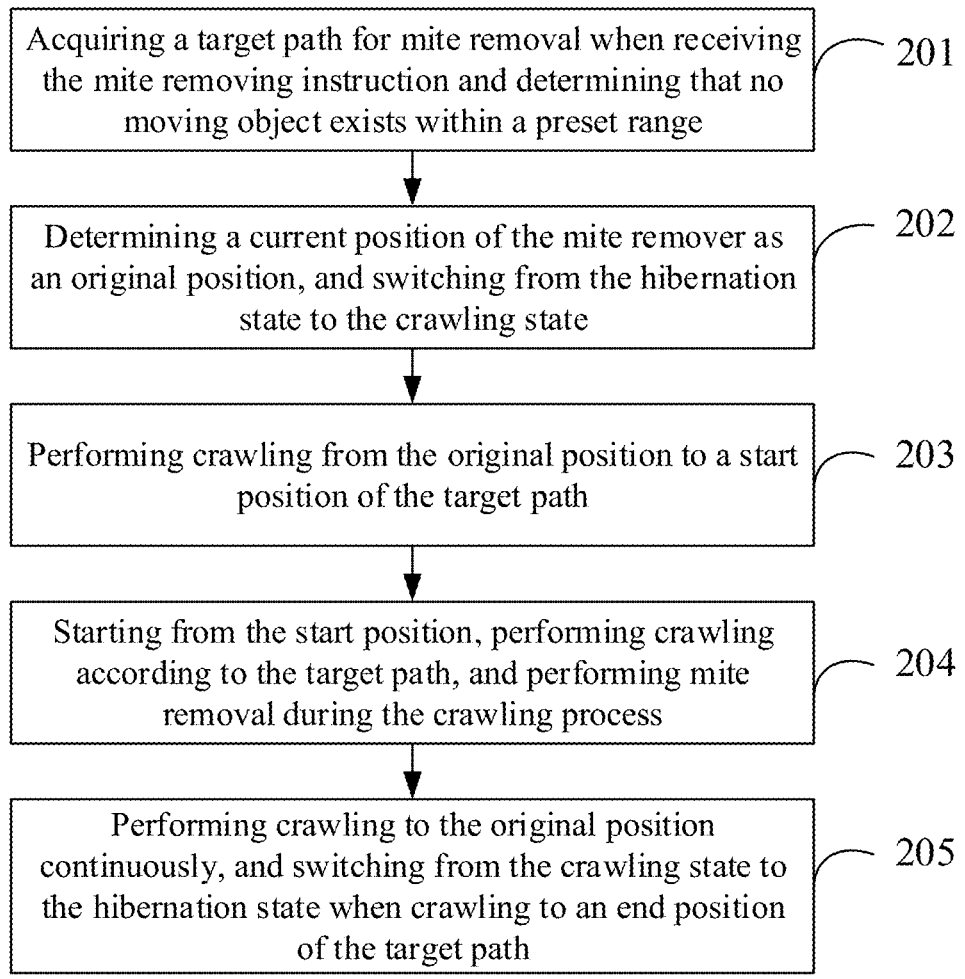
FIG. 2 is a flowchart illustrating a method of removing mites according to some embodiments.

FIG. 2 is a flowchart illustrating a method of removing mites according to some embodiments, which is applicable to a crawling mite remover. As illustrated in FIG. 2, the method comprises the following steps.

In step 201, when the mite removing instruction is received and it is determined that no moving object exists within a preset range, a target path for mite removal is acquired.

Regarding the mite removing instruction: the mite removing instruction is an instruction that instructs a mite remover to perform mite removal. For example, the mite remover receives a mite removing instruction sent by a terminal, or the mite remover is configured to start mite removal at a preset time, and when it is at the preset time, the mite remover receives a mite removing instruction.

Regarding the preset range: the preset range may be a circular range centered on the mite remover, for example, a circular area with a radius of 3 meters centered on the mite remover.

Regarding the moving object: the moving object may be a person or a pet. Because the mite remover will affect the moving object within the preset range when performing mite removal, it is necessary to detect whether a moving object exists within the preset range of the mite remover when it is at a mite removal time.

When receiving the mite removing instruction, it indicates that the mite remover is about to perform mite removal. When it is determined that no moving object exists within the preset range, it indicates that the mite remover does not affect any moving object when performing mite removal. When the mite removing instruction is received and it is determined that no moving object exists within the preset range, it is determined that mite removal can be started, and a target path for mite removal needs to be acquired.

The process of detecting a moving object may be determined by receiving a detection result sent by a detection device, or may further be determined by a detection device provided by the mite remover itself.

Figure 3:
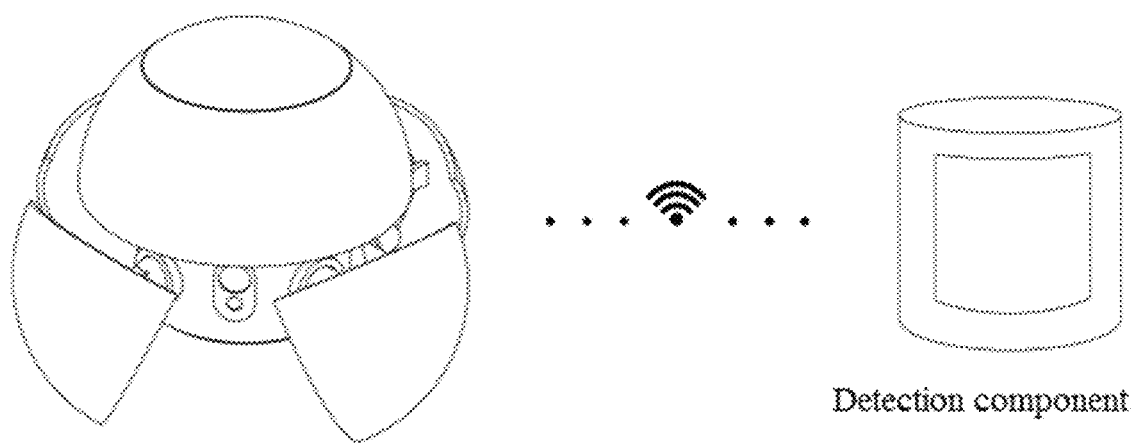
FIG. 3 is a schematic diagram illustrating a communication connection between a mite remover and a detection device according to some embodiments.

In some embodiments of the present disclosure, as illustrated in FIG. 3, the mite remover establishes a communication connection with a detection device. The detection device is configured to detect whether a moving object exists within the preset range of the mite remover. Step 201 may comprise: the mite remover sends a detection result acquisition request to the detection device, the detection device sends a detection result to the mite remover in response to the detection result acquisition request, and the mite remover receives the detection result sent by the detection device.

The detection device may be a body sensor or a camera. The detection device and the mite remover are disposed in the same space.

For example, the mite remover is placed in a bedroom, and the body sensor is also placed in the bedroom. The body sensor detects whether a moving object exists in the bedroom. If no moving object exists in the bedroom, the body sensor obtains a first detection result. If a moving object exists, the body sensor obtains a second detection result. The body sensor detects whether a moving object exists in the bedroom in real time, and sends the current detection result to the mite remover upon receiving a detection result acquisition request sent by the mite remover.

In some embodiments of the present disclosure, the mite remover itself is provided with a detection device. Step 201 may comprise: the mite remover detects whether a moving object exists within the preset range of the mite remover through the detection device. The detection device may be a body sensor or a camera.

Regarding the detection timing, in some embodiments, when it is at the preset time, it is detected whether a moving object exists within the preset range of a mite remover.

The preset time may be a mite removing time set by a user. For example, the user sets the mite remover to perform mite removal at 8 am. That is, the preset time is 8 am. The preset time may be set by the user on the mite remover. Or, the preset time may be set by the user through a terminal connected to the mite remover.

For example, the detection device provided on the mite remover is a body sensor. When it is not at the preset time, the body sensor of the mite remover is turned off. When the preset time is reached, the mite remover starts the body sensor to detect whether a moving object exists within the preset range, and obtains a detection result.

In some embodiments of the present disclosure, when the mite removing instruction is received, it is detected whether a moving object exists within the preset range of the mite remover.

In addition, the detection results corresponding to the presence of a moving object within the preset range of the mite remover comprise: a first detection result and a second detection result. The first detection result indicates that no moving object exists within the preset range of the mite remover. The second detection result indicates that a moving object exists within the preset range of the mite remover.

Regarding the process of acquiring a target path for mite removal, the target path is a path that the mite remover needs to crawl on a surface of an object when performing mite removal on the object. The generation of the target path is determined according to the surface of the object that requires mite removal. It is necessary to not only ensure that the mite remover can cover the surface of the object when crawling along the target path, but further avoid repeated mite removal on a certain area of the surface of the object. The target path may be set by the user, or may be obtained through scanning by the mite remover the object that needs mite removal.

In some embodiments of the present disclosure, the mite remover scans a surface of an object, determines the size of the surface of the object that requires mite removal, calculates a target path, stores the target path, and reads the stored target path when the mite removing instruction is received.

Figure 4:
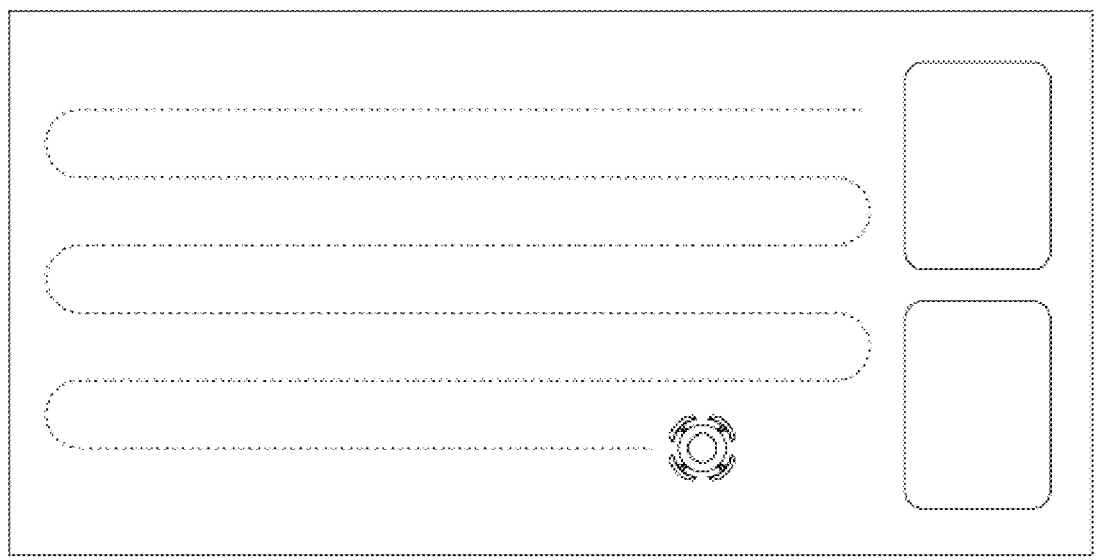
FIG. 4 is a schematic diagram illustrating a target path according to some embodiments.

For example, the mite remover needs to perform mite removal on a bed, and scans a surface of the bed in advance and obtain that a mite remover area is a rectangle with a length of 2 meters and a width of 1.8 meters. A calculated target path is illustrated in FIG. 4. The target path is indicated by the dotted line in the figure.

In some other embodiments, the user inputs the size of the surface of the object that requires mite removal to the mite remover through a terminal connected to the mite remover or an input device comprised in the mite remover. The mite remover determines a target path according to the size, stores the target path, and reads the target path when the mite removing instruction is received.

In step 202, a current position of the mite remover is determined as an original position, and the hibernation state is switched to the crawling state.

The mite remover according to the embodiments of the present disclosure comprises two states.

1. Hibernation state: the mite remover is stationary. In this state, the mite remover cannot crawl on the surface of the object, and cannot perform mite removal on the surface of the object. For example, when the mite remover is in a hibernation state, the mite remover is stationary at a position, the crawling function of the mite remover is turned off, and the mite removal function is turned off, which can save power consumption.

2. Crawling state: the mite remover can crawl on the surface of the object, and the mite remover can perform mite removal on the surface of the object. For example, when the mite remover is switched to the crawling state, the mite remover can crawl on the surface of the object and can perform mite removal on the surface of the object.

Before the mite remover receives the mite removing instruction, the mite remover is in a hibernation state and stands still at the current position of the mite remover. When the mite remover receives the mite removing instruction, it indicates that the mite remover is about to start to perform mite removal. Since the mite remover needs to crawl on the surface of the object when performing mite removal, the mite remover needs to switch from the hibernation state to the crawling state.

When the mite remover is in a hibernation state, the current position of the mite remover may be a charging position of the mite remover, a storage position of the mite remover, or any other position. In order to prevent the mite remover from being placed randomly after completing mite removal, when the mite removing instruction is received, the mite remover records the current position as the original position to ensure that the mite remover can return to the current position where the mite remover is in a hibernation state after completing mite removal.

For example, when the mite remover is in a hibernation state, the position is the charging position of the mite remover where the mite remover can be charged, and the mite remover records the charging position so that the mite remover can crawl back to the charging position for charging according to the recorded position after completing mite removal.

In step 203, crawling is performed from the original position to a start position of the target path.

Because the original position of the mite remover is different from the start position of the target path, the mite remover needs to crawl from the original position to the start position of the target path before performing mite removal according to the target path.

In some embodiments of the present disclosure, the mite remover comprises a positioning component. The positioning component determines the original position, determines the start position according to the target path, plans a crawling path from the original position to the start position for the mite remover to crawl from the original position to the start position.

It should be noted that the embodiment of the present disclosure is described by taking the case where the original position of the mite remover and the start position of the target path are different as an example. In another embodiment, the original position of the mite remover and the start position of the target path coincide with each other, then after performing step 202, step 204 is performed, and step 203 is not required to be performed.

In step 204, starting from the start position, crawling is performed according to the target path, and mite removal is performed during the crawling process.

The mite remover crawls along the target path on the surface of the object starting from the start position of the target path, and perform mite removal on the surface of the object during the crawling process.

In some embodiments of the present disclosure, the mite remover is provided with an ultraviolet lamp. During the crawling process of the mite remover, the surface of the object is irradiated with the ultraviolet lamp, and mites are killed by ultraviolet rays.

In some embodiments of the present disclosure, the mite remover is provided with a dust suction component. During the crawling process of the mite remover, the dust suction component generates suction and sucks out dust on the surface of the object, thereby sucking mites into the machine.

In some embodiments of the present disclosure, the mite remover is provided with an ultraviolet lamp and a dust suction component. During the crawling process, the ultraviolet lamp emits ultraviolet rays to irradiate the surface of the object and kill mites. The dust suction component generates suction to suck mites into the machine, thereby performing mite removal on the surface of objects more effectively.

In step 205, when crawling to an end position of the target path, crawling is continuously performed to the original position, and the crawling state is switched to the hibernation state.

The mite remover crawling to the end position of the target path indicates that the mite remover has completed mite removal, and the mite remover crawls to the original position according to the recorded original position. When crawling to the original position, the mite remover no longer needs to crawl, then is switched from the crawling state to the hibernation state, and stands still at the original position.

In some embodiments of the present disclosure, the mite remover switches from the hibernation state to the crawling state, completes mite removal according to the target path, crawls to the original position, and then is switched to the hibernation state. In order to facilitate the follow-up check of the mite removal history of the mite remover, the mite remover will record each mite removal after mite removal is completed.

For each mite removal recorded by the mite remover, in some embodiments, during the mite removal process, when crawling to the start position of the target path, the mite remover determines the time when crawling to the start position as a start time of mite removal, and when crawling to the end position of the target path, determines the time when crawling to the end position as an end time of mite removal, and generates a mite removing log.

The mite remover crawling to the start position of the target path indicates that the mite remover starts mite removal. That is, the time when reaching the start position is the start time of mite removal. The mite remover crawling to the end position of the target path indicates that the mite remover ends mite removal. That is, the time when reaching the end position is the end time of mite removal. A time interval between the start time of mite removal and the end time of mite removal is a mite removal duration. Accordingly, the mite removing log comprises the start time of mite removal and the end time of mite removal. Or, the mite removing log comprises the start time of mite removal and the mite removal duration.

For the generated mite removing log, in some embodiments, after generating a mite removing log, the mite remover stores the mite removing log; or, the mite remover uploads the mite removing log to a connected server, and the server stores the mite removing log.

In some embodiments of the present disclosure, the mite remover sends the mite removing log to a connected terminal, and the terminal displays the mite removing log. The terminal establishes a communication connection with the mite remover. The terminal may be a mobile phone, a tablet computer, a notebook computer, and other devices. After receiving the mite removing log, the terminal displays the mite removing log, and the user can check the operation status of the mite remover.

In some embodiments of the present disclosure, the terminal sends a mite removing log acquisition request to the mite removal, and after receiving the request, the mite remover sends the mite removing log to the terminal.

Figure 5:
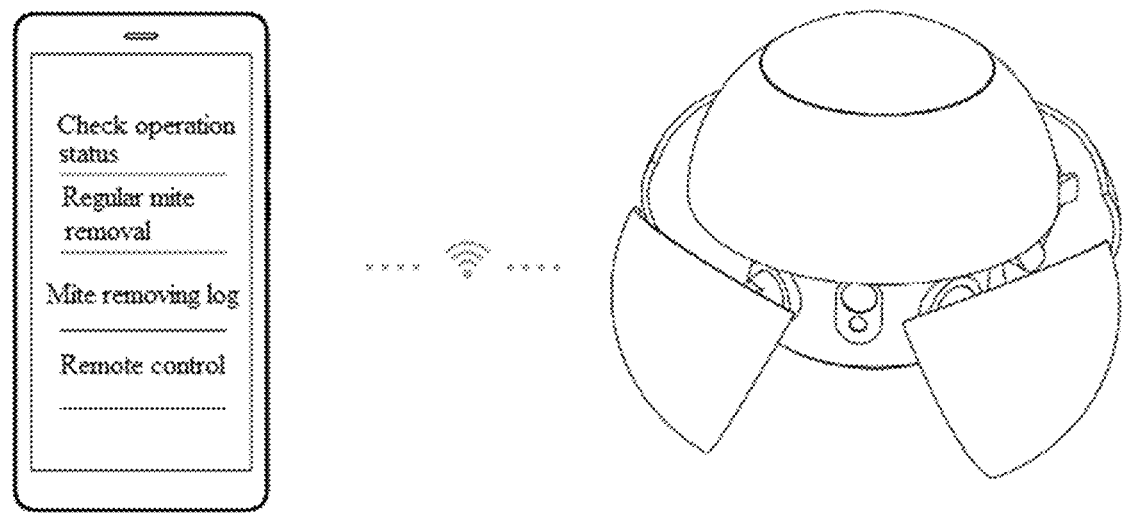
FIG. 5 is a schematic diagram illustrating a communication connection between a mite remover and a terminal according to some embodiments.

As illustrated in FIG. 5, the terminal establishes a communication connection with the mite remover. Through this communication connection, the terminal can view the mite removing log of the mite remover and learn the mite removal history of the mite remover; can view the state of the mite remover anytime to see whether or not mite removal is currently in progress; can set a regular mite removal for the mite remover, where when it is at a preset time set by the user, the mite remover will start mite removal; and the mite remover can further be remotely controlled and is remotely operated to switch from the hibernation state to the crawling state, or switch from the crawling state to the hibernation state.

In the method according to the embodiment of the present disclosure, when the mite removing instruction is received and it is determined that no moving object exists within a preset range, a target path for mite removal is acquired, a current position of a mite remover is determined as an original position, a hibernation state is switched to a crawling state, crawling is performed from the original position to a start position of the target path, starting from the start position, crawling is performed according to the target path, mite removal is performed during the crawling process, when crawling to an end position of the target path, crawl is continuously performed to the original position, and the crawling state is switched to the hibernation state. In the method of removing mites according to the embodiments of the present disclosure, when it is the time for mite removal, the mite remover automatically starts mite removal without user operation, which is convenient for users. The mite remover can crawl to the original position after completing mite removal, which realizes automatic storage.

In addition, after each mite removal is completed, a mite removing log is generated to record the mite removal status, so that the user can read the mite removing log and view the mite removal history of the mite remover.

It should be noted that the embodiment of the present disclosure is described by taking an example of receiving the mite removing instruction and determining that no moving object exists within the preset range of the mite remover. In another embodiment, when it is determined that a moving object exists within the preset range of the mite remover, whether a moving object exists within the preset range of the mite remover is detected repeatedly, and the subsequent steps are performed until no moving object exists within the preset range of the mite remover.

In the method and the mite remover according to the embodiments of the present disclosure, when receiving a mite removing instruction, a target path for mite removal is acquired, a hibernation state is switched to a crawling state, crawling is performed according to the target path, mite removal is performed during the crawling process, and when crawling to an end position of the target path, the crawling state is switched to the hibernation state. The method of removing mites according to the embodiment of the present disclosure does not require user operation during the mite removal process, and can automatically complete mite removal, which is convenient for users.

When the mite removing instruction is received and it is determined that no moving object exists within a preset range, a target path for mite removal is acquired, a current position of the mite remover is determined as an original position, a hibernation state is switched to a crawling state, crawling is performed from the original position to a start position of the target path, starting from the start position, crawling is performed according to the target path, mite removal is performed during the crawling process, when crawling to an end position of the target path, crawling is continuously performed to the original position, and the crawling state is switched to hibernation state. In the method of removing mites according to the embodiments of the present disclosure, when the time for mite removal is reached, the mite remover automatically starts mite removal without user operation, which is convenient for users. The mite remover can crawl to the original position after mite removal is completed, which realizes automatic storage.

In addition, after each mite removal is completed, a mite removing log is generated to record the mite removal situation, so that the user can view the mite removal situation of the mite remover through the mite removing log.

Figure 6:
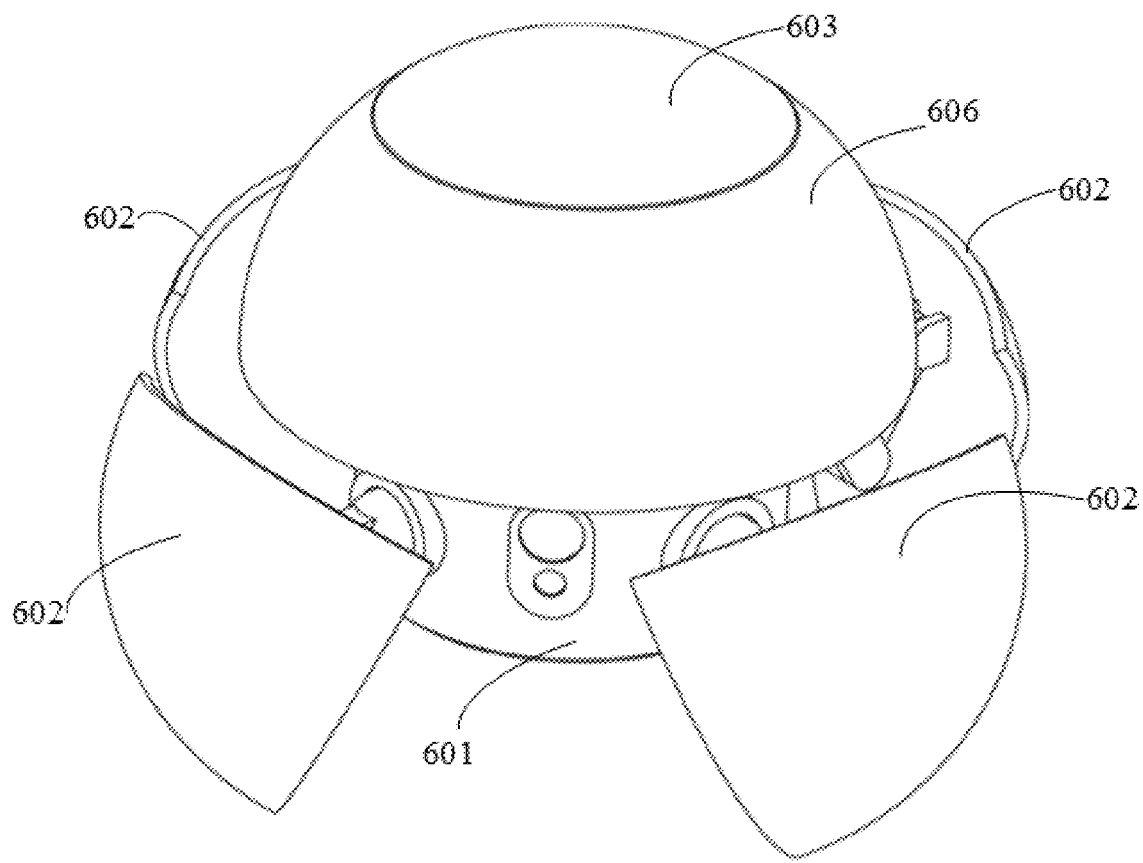
FIG. 6 is a schematic structural diagram of a mite remover according to some embodiments.

FIG. 6 is a schematic structural diagram of a mite remover according to some embodiments. As illustrated in FIG. 6, the mite remover comprises a processor, a first motor, a body 601, and a plurality of legs 602. The processor and the first motor are disposed inside the body 601. The processor is connected to the first motor. The first motor is connected to the plurality of legs 602.

The processor is a control center of the mite remover, and is configured to control various electrical components of the mite remover. The first motor is configured to drive the legs 602 to perform a telescopic movement. The body 601 is configured to carry various functional components except the legs 602 of the mite meter. The mite remover can crawl through the telescopic movement of the leg 602s, and drive other components except the legs 602 to move during the crawling. The plurality of legs 602 is disposed on a side of the body 601. The body 601 can be supported by the plurality of legs 602.

The processor is electrically connected to the first motor. The first motor can be controlled to rotate through the electrical connection. The first motor is connected to the plurality of legs 602. When the first motor rotates, the plurality of legs 602 can be driven to perform a telescopic movement.

Figure 7:
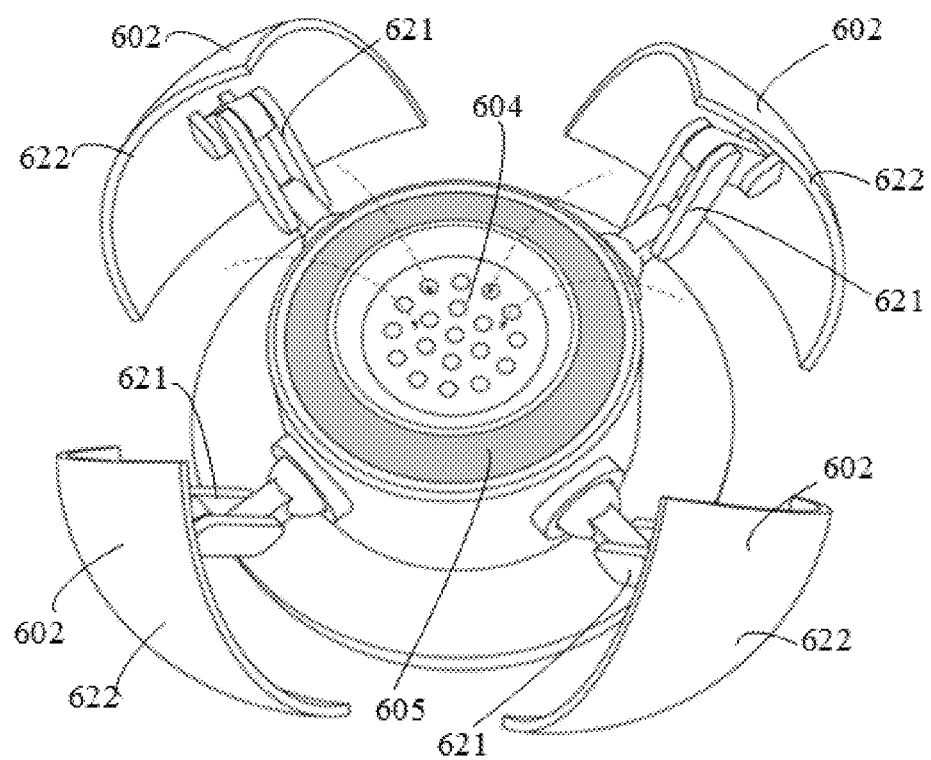
FIG. 7 is a schematic structural diagram of another mite remover according to some embodiments.

In order to facilitate the crawling of the mite remover, in some embodiments, the plurality of legs 602 is arranged on a side of the body 601 in a certain order. The quantity of the plurality of legs 602 is an even number. As illustrated in FIG. 7, the number of the plurality of legs 602 may be four, and the side of the body 601 is circular, then the four legs 602 are arranged regularly on the side of the body 601.

In order to facilitate driving the plurality of legs 602 to perform a telescopic movement and enable the mite remover to crawl, in some embodiments, the mite remover may comprise a plurality of first motors. The number of the first motors and the number of the legs 602 are equal. The processor is electrically connected to the plurality of first motors. Each first motor is connected to one leg 602. When the processor drives any of the first motors, a corresponding leg 602 is driven to perform the telescopic movement.

For the process of the mite remover performing mite removal on the surface of the object, the processor sends a movement signal to the first motor, the first motor drives the plurality of legs 602 to perform the telescopic movement based on the movement signal, the plurality of legs 602 is in contact with the surface of the object, the plurality of legs 602 moves relative to the surface of the object, driving the body 601 to move on the surface of the object, and the body 601 performs mite removal on the surface of the object. The movement signal indicates that the mite remover needs to crawl. After receiving the movement signal, the first motor determines that the plurality of legs 602 needs to be driven to perform a telescopic movement.

Regarding the body 601 performing mite removal on the surface of the object, in some embodiments, the body 601 is provided with a mite removing component. When the legs 602 drive the body 601 to move on the surface of the object, the mite removing component performs mite removal on the surface of the object.

Regarding the motor driving the plurality of legs 602 to perform the telescopic movement, in some embodiments, the first motor is connected to a first gear, a first end of each leg 602 is connected to a second gear set, and the first gear is engaged with one gear in each of the second gear sets. When the first motor rotates, the first gear is driven to rotate, driving the second gear set to rotate, thereby driving the plurality of legs 602 to perform the telescopic movement.

The mite remover according to the embodiment of the present disclosure comprises the processor, the body 601, the first motor, and the plurality of legs 602. The plurality of legs 602 is disposed on a side of the body 601. The processor and the first motor are disposed inside the body 601. The processor is connected to the first motor. The first motor is connected to the plurality of legs 602. The processor sends a movement signal to the first motor. The first motor drives the plurality of legs 602 to perform the telescopic movement based on the movement signal, driving the body 601 to move on the surface of the object. The body 601 performs mite removal on the surface of the object. When performing mite removal, the mite remover can automatically move on the surface of the object through the legs 602 without user operation, which is convenient for users.

In some embodiments of the present disclosure, as illustrated in FIG. 6 and FIG. 7, a dust box 603 is provided at the top of the body 601, a dust suction port 604 is provided at the bottom of the body, a passage is provided inside the body 601, a turbine is provided in the passage, and the interior of the dust box 603, the passage, and the dust suction port 604 communicate with each other.

The dust box 603 is configured to accommodate sucked dust. The dust suction port 604 may be provided with a plurality of round holes for dust to pass through.

In addition, the dust box 603 can be connected to the body 601 by screws or can be fixed to the body 601 by a buckle, so that the dust box 603 and the body 601 are fixed together. That is, when it is necessary to clean up the dust in the dust box 603, it is convenient to detach the dust box 603 from the body 601.

When the body 601 performs mite removal on a surface of an object, the turbine rotates to generate suction to suck the dust on the surface of the object through the dust suction port 604 and suck the same into the dust box 603 through the passage.

In addition, a third motor is provided in the body 601. The third motor is connected to the turbine. The processor is electrically connected to the third motor. Then, the processor drives the third motor to rotate to drive the turbine to rotate.

In some embodiments of the present disclosure, as illustrated in FIG. 7, an ultraviolet lamp 605 is provided at the bottom of the body 601. When the body 601 moves on a surface of an object, the ultraviolet lamp 605 irradiates the surface of the object and uses ultraviolet rays to kill mites.

In some embodiments of the present disclosure, as illustrated in FIG. 7, a dust box 603 is provided at the top of the body 601, a dust suction port 604 and an ultraviolet lamp 605 are provided at the bottom, a passage is provided inside the body 601, a turbine is provided in the passage, and the interior of the dust box 603, the passage and the dust suction port 604 are in communication.

The ultraviolet lamp 605 may have a ring shape and is disposed on the outer side of the dust suction port 604.

When the body 601 performs mite removal on a surface of an object, the ultraviolet lamp 605 emits ultraviolet rays to irradiate the surface of the object and kill mites. At the same time, the turbine rotates to generate suction to suck the dust and mites on the surface of the object through the dust suction port 604 and suck the same into the dust box 603 through the passage, thereby performing mite removal on the surface of the object more effectively.

In the mite remover according to the embodiment of the present disclosure, when mite removal is performed on a surface of an object, the dust on the surface of the object is sucked into the dust box 603, thereby sucking the mites into the machine, or ultraviolet rays are adopted to kill the mites to effectively perform mite removal on the surface of the object.

Figure 8:
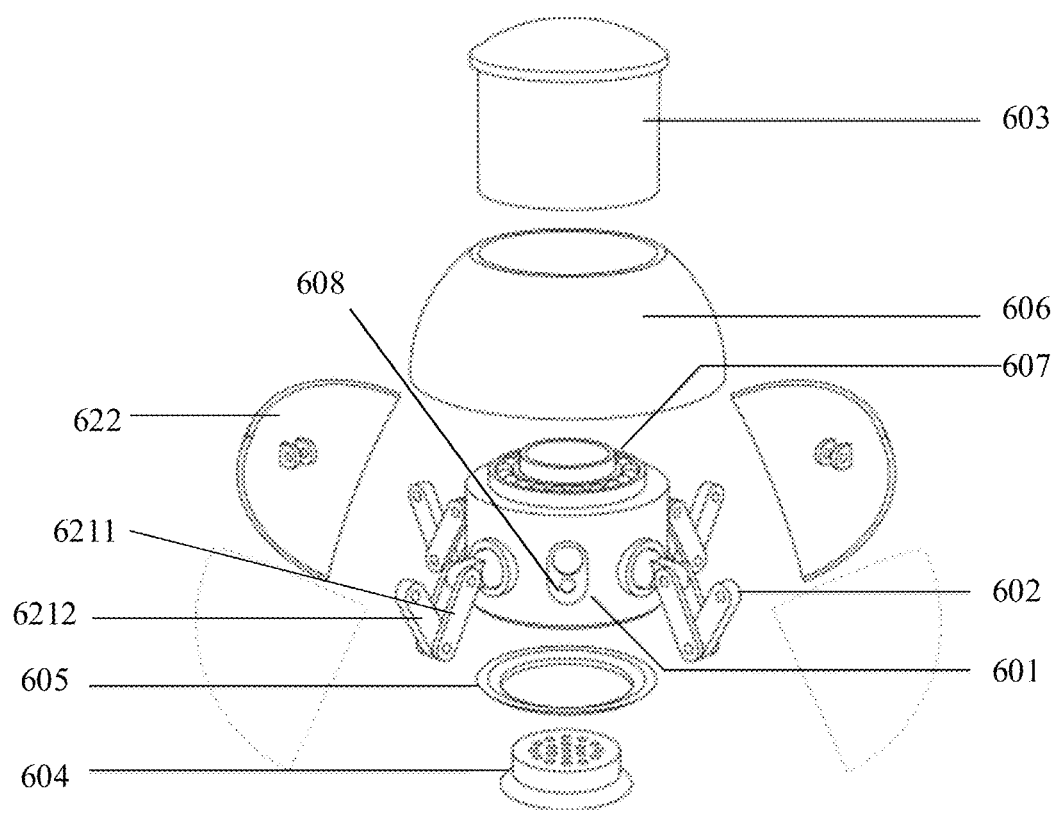
FIG. 8 is a schematic structural diagram of another mite remover according to some embodiments.

In some embodiments of the present disclosure, as illustrated in FIG. 6, an upper shell 606 is provided on an outer side of the dust box 603. As illustrated in FIG. 8, the body 601 is provided with a bearing 607 and a second motor. The upper shell 606 is connected to the body 601 through the bearing 607.

The upper shell 606 is a casing wrapping the outer side of the body 601, and can protect the body 601. The second motor is connected to the bearing 607.

The dust box 603 is connected to the upper shell 606. Since the upper shell 606 is connected to the body 601 through the bearing 607, the body 601 can rotate relative to the upper shell 606 and the dust box 603.

The processor sends a steering signal to the second motor. Based on the steering signal, the second motor drives the bearing 607 to rotate and drive the body 601 to rotate relative to the upper shell 606 to steer on the surface of the object.

Figure 9:
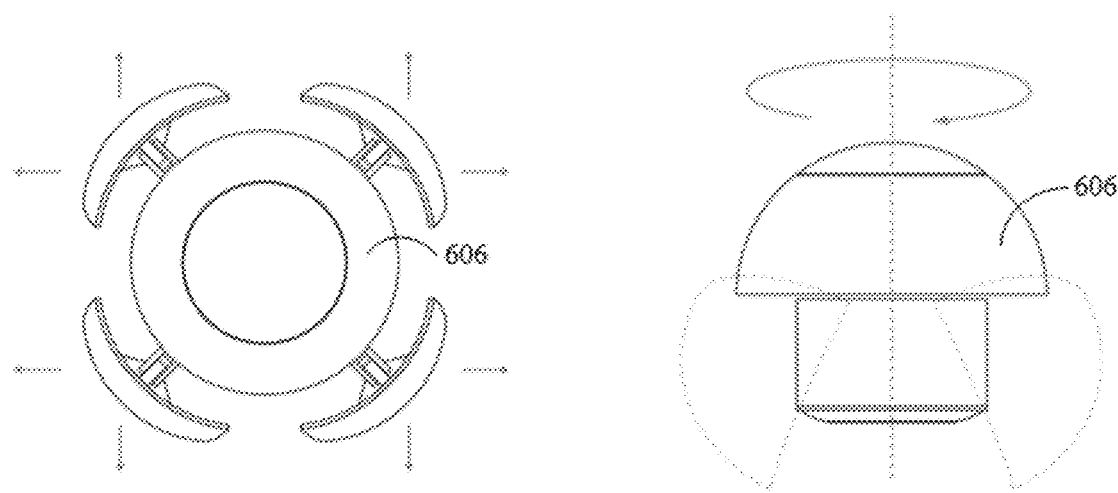
FIG. 9 is a schematic structural diagram of another mite remover according to some embodiments.

As illustrated in FIG. 9, when the mite remover is required for steering, the second motor drives the bearing 607 to rotate, the upper shell 606 and the dust box 603 remain stationary, and the body 601 rotates relative to the upper shell 606 and drives the plurality of legs 602 to rotate to achieve the steering of the mite remover on the surface of the object.

In addition, when the mite remover is steering on the surface of the object, the second motor drives the bearing 607 to rotate, the upper shell 606 and the dust box 603 remain stationary, the body 601 rotates relative to the upper shell 606, the first motor drives the plurality of legs 602 to perform the telescopic movement, and then the plurality of legs 602 moves on the surface of the object, thereby achieving the steering of the mite remover on the surface of the object without user operation.

Figure 10:
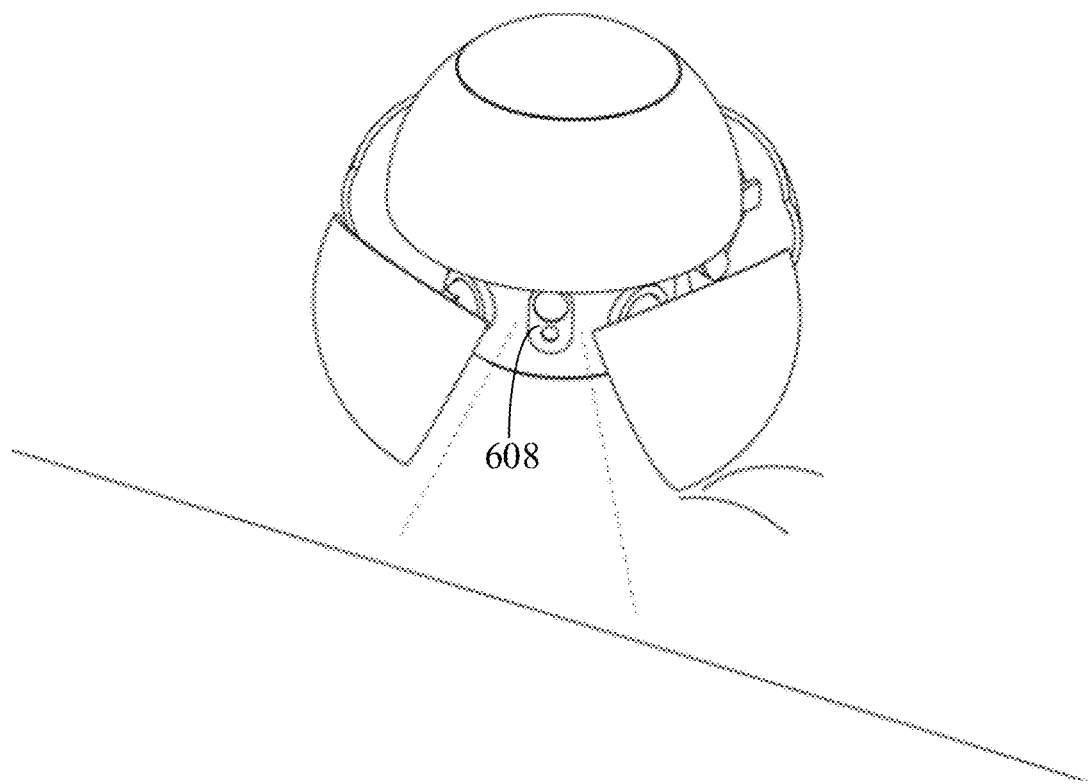
FIG. 10 is a schematic structural diagram of another mite remover according to some embodiments.

In some embodiments of the present disclosure, as illustrated in FIG. 10, the body 601 is provided with a sensor 608. The sensor 608 is connected to the processor.

The sensor 608 is configured to detect the position of the mite remover relative to the object. The sensor 608 may be an infrared sensor 608, a distance sensor 608, or a color sensor 608.

For example, during the crawling process of the mite remover, the color sensor 608 determines the color in front of the mite remover in real time. When the difference in color changes is greater than a threshold, it is determined that the mite remover crawls to the edge of the surface of the object.

When the mite remover is crawling, the sensor 608 detects a position of the mite remover relative to the object in real time. When it is determined that the mite remover is located at an edge of the object, the sensor sends a steering signal to the processor, and the processor sends the steering signal to the second motor. The sensor 608 can identify an edge of the object, so that the mite remover can complete automatic steering at the edge of the object.

In some embodiments of the present disclosure, the mite remover comprises a communication module. The communication module is connected to the processor.

The communication module is configured to perform network signal transmission. For example, the mite remover can establish network communication with a terminal through the communication module.

The communication module receives a target path sent by the terminal, and sends the target path to the processor.

The target path is a path along which the mite remover needs to crawl so as to perform mite removal on an object, which may be set by a user, or may be obtained after the mite remover scans the object that needs mite removal.

The communication module sends the received target path to the processor. The processor can subsequently control various electrical components of the mite remover according to the target path, so that the mite remover can perform mite removal according to the target path.

In addition, when a user needs the mite remover to perform mite removal, a target path is sent to the communication module through a terminal, and the communication module receives the target path. Alternatively, the mite remover sends a request for acquiring target path to the terminal through the communication module, the terminal receives the request for acquiring target path, and sends the target path to the communication module, and the communication module receives the target path.

In some embodiments of the present disclosure, the body 601 further comprises a positioning component. The positioning component is connected to the processor.

The positioning component is configured to acquire position information of the mite remover, and sends the acquired position information to the processor through the connection with the processor.

The positioning component detects a current position of the mite remover and sends the same to the processor. The processor controls the first motor according to a positional relationship between the position and the target path.

During the crawling process of the mite remover according to the target path, the positioning component acquires the position of the mite remover in real time and sends the position of the mite remover to the processor. When a deviation exists between the current position and the target path, the processor controls the first motor to move. Through the positioning component, the mite remover can crawl along the target path, so that the mite remover can automatically perform mite removal on the surface of the object.

In some embodiments of the present disclosure, as illustrated in FIG. 7, each leg 602 comprises a connector 621 and a lower shell 622. The first motor is connected to the connector 621. The connector 621 is connected to the lower shell 622.

The connector 621 and the lower shell 622 may be fixedly connected together. Or the connector 621 and the lower shell 622 may rotate relative to each other.

The first motor drives the connector 621 to perform a telescopic movement, driving the lower shell 622 to move on the surface of the object. The body 601 performs mite removal on the surface of the object. When the mite remover is crawling, the first motor drives the connector 621 to perform a telescopic movement. The connector 621 drives the lower shell 622 to move. The lower shell 622 contacts the surface of the object and moves on the surface of the object.

In some embodiments of the present disclosure, an upper shell 606 is provided on an outer side of the dust box 603. The upper shell 606 is hemispherical. The lower shells 622 of the plurality of legs 602 are arc-shaped. The lower shell 622 is arc-shaped such that lower shells 622 of the plurality of legs 602 can form a hemisphere.

Figure 11:
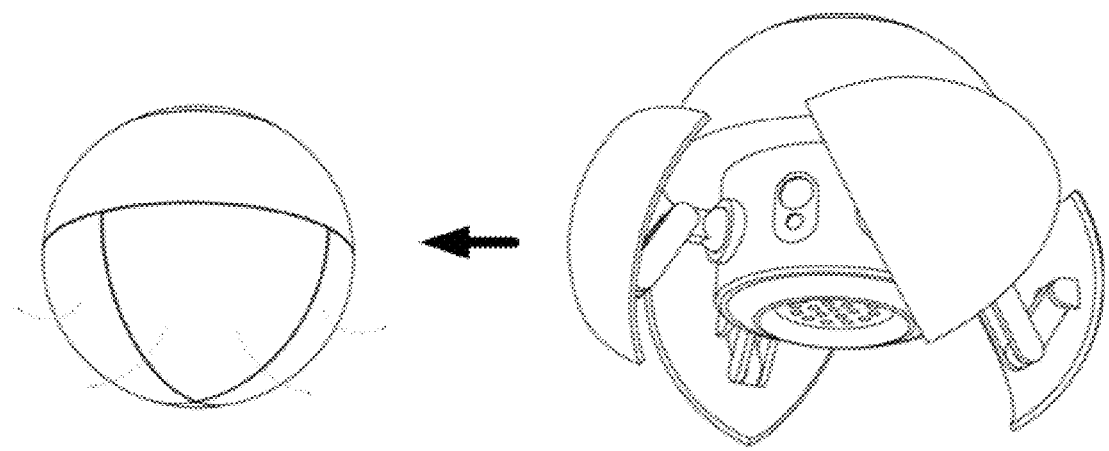
FIG. 11 is a schematic structural diagram of another mite remover according to some embodiments.

As illustrated in FIG. 11, the left part illustrates the mite remover in a hibernation state, and the right part illustrates the mite remover in a crawling state. When the mite remover switches to the hibernation state, the first motor drives the connectors 621 of the plurality of legs 602 to telescope, driving the lower shells 622 of the plurality of legs 602 to fit on the side of the body 601 and contact the upper shell 606. The upper shell 606 and the lower shells 622 of the plurality of legs 602 form a sphere, wrapping the body 601 within the sphere.

In some embodiments of the present disclosure, as illustrated in FIG. 8, the connector 621 comprises a first joint 6211 and a second joint 6212. The first motor is connected to the first joint 6211. The first joint 6211 is connected to the second joint 6212. The second joint 6212 is connected to the lower shell 622. A third motor is provided between the first joint 6211 and the second joint 6212.

The third motor can drive the second joint 6212 to rotate relative to the first joint 6211. The first motor can drive the first joint 6211 to rotate. When the mite remover is crawling, the processor sends a movement signal to the first motor and the third motor. The first motor drives the first joint 6211 to rotate according to the movement signal. The third motor drives the second joint 6212 to rotate relative to the first joint 6211 according to the movement signal. The second joint 6212 drives the lower shell 622 to move, so that the telescopic movement of the leg 602 is realized.

The mite remover according to the embodiment of the present disclosure may be as illustrated in FIG. 8. The processor may send a movement signal to the first motor and the third motor when receiving a mite removing instruction. The first motor and the third motor drive the first joint 6211 and the second joint 6212 to perform a telescopic movement based on the movement signal, driving the lower shell 622 to move and thereby driving the body 601 to move on the surface of the object according to the target path. During the movement, the ultraviolet lamp 605 irradiates the surface of the object and mite removal is performed by the ultraviolet rays emitted by the ultraviolet lamp 605. At the same time, the turbine rotates to suck dust on the surface of the object into the dust box 603 through the passage from the dust suction port 604. The positioning component detects a first position of the mite remover and sends the same to the processor. The processor controls the first motor according to a positional relationship between the first position and the target path, so as to keep the mite remover move according to the target path to avoid deviating from the target path.

In addition, the sensor 608 detects a position of the mite remover relative to the object, and when it is determined that the mite remover is located at an edge of the object, sends a steering signal to the processor. The processor sends the steering signal to the second motor. The second motor drives the bearing 607 to rotate based on the steering signal, driving the body 601 to rotate relative to the upper shell 606 and to steer on the surface of the object.

Figure 12:
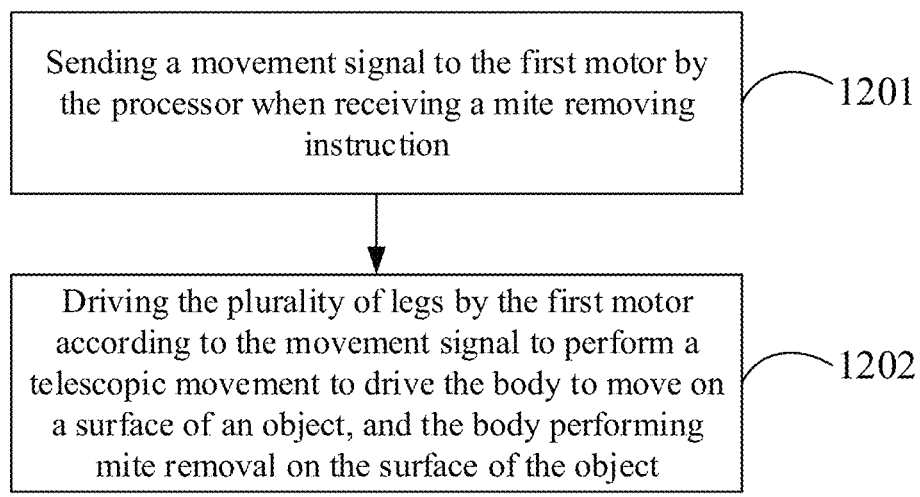
FIG. 12 is a flowchart illustrating a method of removing mites according to some embodiments.

FIG. 12 is a flowchart illustrating a method of removing mites according to some embodiments, which is applicable to a mite remover. As illustrated in FIG. 12, the mite remover comprises a processor, a body, a first motor, and a plurality of legs. The plurality of legs is disposed on a side of the body. The processor and the first motor are disposed inside the body. The processor is connected to the first motor. The first motor is connected to the plurality of legs. The method comprises the following steps.

In step 1201, when receiving a mite removing instruction, the processor sends a movement signal to the first motor.

In step 1202, according to the movement signal, the first motor drives the plurality of legs to perform a telescopic movement to drive the body to move on a surface of an object, and the body performs mite removal on the surface of the object.

In the method according to the embodiments of the present disclosure, the mite remover comprises a processor, a body, a first motor, and a plurality of legs. The plurality of legs is disposed on a side of the body. The processor and the first motor are disposed inside the body. The processor is connected to the first motor. The first motor is connected to the plurality of legs. When receiving a mite removing instruction, the processor sends a movement signal to the first motor. According to the movement signal, the first motor drives the plurality of signals to perform a telescopic movement, driving the body to move on the surface of the object, and the body performs mite removal on the surface of the object. During mite removal, the mite remover can automatically move on the surface of the object through the legs without user operation, which is convenient for users.

In some embodiments of the present disclosure, a dust box is provided at the top of the body, and a dust suction port is provided at the bottom of the body. A passage is provided inside the body. A turbine is provided in the passage. The interior of the dust box, the passage, and the dust suction port communication with each other. The body performing mite removal on the surface of the object comprises:

the turbine rotates to suck the dust on the surface of the object into the dust box through the passage from the dust suction port.

In some embodiments of the present disclosure, an ultraviolet lamp is provided at the bottom of the body. The body performing mite removal on the surface of the object comprises:

the ultraviolet lamp irradiates the surface of the object, and ultraviolet rays emitted by the ultraviolet lamp perform mite removal.

In some embodiments of the present disclosure, the mite remover further comprises a detection component. The detection component is connected to the processor. The method further comprises:

the processor controls the detection component to detect whether a moving object exists within a preset range of the mite remover; and when the processor receives the mite removing instruction and determines that no moving object exists within the preset range, the processor sends a movement signal to the first motor.

Regarding the timing for detection, in some embodiments, when it is at a preset time, the processor controls the detection component to detect whether a moving object exists within the preset range of the mite remover.

In some embodiments of the present disclosure, when the processor receives the mite removing instruction, the processor controls the detection component to detect whether a moving object exists within the preset range of the mite remover.

In addition, the detection component obtains a detection result after detecting whether a moving object exists within the preset range of the mite remover, and sends the detection result to the processor. The processor determines whether a moving object exists within the preset range according to the detection result.

In addition, the detection result corresponding to whether a moving object exists within the preset range of the mite remover comprise: a first detection result and a second detection result. The first detection result indicates that no moving object exists within the preset range. The second detection result indicates that a moving object exists within the preset range of the mite remover.

When the processor receives the mite removing instruction and receives the first detection result, that is, when no moving object exists within the preset range of the mite remover, the processor sends a movement signal to the first motor. When the processor receives the mite removing instruction and the second detection result, that is, when a moving object exists within the preset range of the mite remover, the processor continues to control the detection component to perform detection until the processor receives the first detection result. Then the processor sends a movement signal to the first motor.

In some embodiments of the present disclosure, an upper shell is provided on an outer side of the dust box. The body is provided with a bearing and a second motor. The upper shell is connected to the body through the bearing. The body is provided with a sensor. The sensor is connected to the processor. The method further comprises:

the sensor detects a position of the mite remover relative to the object;

when it is determined that the mite remover is located at an edge of the object, a steering signal is sent to the processor;

the processor sends the steering signal to the second motor; and according to the steering signal, the second motor drives the bearing to rotate and drive the body to rotate relative to the upper shell and to steer on the surface of the object.

In some embodiments of the present disclosure, the mite remover further comprises a communication module. The communication module is connected to the processor. The method further comprises:

the communication module receives a target path sent by a terminal, and sends the target path to the processor.

In some embodiments of the present disclosure, the body further comprises a positioning component. The positioning component is connected to the processor. The method further comprises:

the positioning component detects a first position of the mite remover and sends the first position to the processor; and the processor controls the first motor according to a positional relationship between the first position and the target path.

The various device components, modules, units, blocks, or portions may have modular configurations, or are composed of discrete components, but nonetheless can be referred to as "modules" in general. In other words, the "components," "modules," "blocks," "portions," or "units" referred to herein may or may not be in modular forms.

Various embodiments of the present disclosure can have one or more of the following advantages.

In the method and the mite remover according to the embodiments of the present disclosure, when receiving a mite removing instruction, a target path for mite removal is acquired, a hibernation state is switched to a crawling state, crawling is performed according to the target path, mite removal is performed during the crawling process, and when crawling to an end position of the target path, the crawling state is switched to the hibernation state. The method of removing mites according to the embodiment of the present disclosure does not require user operation during the mite removal process, and can automatically complete mite removal, which is convenient for users.

When the mite removing instruction is received and it is determined that no moving object exists within a preset range, a target path for mite removal is acquired, a current position of the mite remover is determined as an original position, a hibernation state is switched to a crawling state, crawling is performed from the original position to a start position of the target path, starting from the start position, crawling is performed according to the target path, mite removal is performed during the crawling process, when crawling to an end position of the target path, crawling is continuously performed to the original position, and the crawling state is switched to hibernation state. In the method of removing mites according to the embodiments of the present disclosure, when the time for mite removal is reached, the mite remover automatically starts mite removal without user operation, which is convenient for users. The mite remover can crawl to the original position after mite removal is completed, which realizes automatic storage.

In addition, after each mite removal is completed, a mite removing log is generated to record the mite removal situation, so that the user can view the mite removal situation of the mite remover through the mite removing log.

Other implementation solutions of the present disclosure will be apparent to those skilled in the art from consideration of the specification and practice of the present disclosure. This disclosure is intended to cover any variations, uses, or adaptations of the present disclosure following the general principles thereof and including such departures from the present disclosure as come within known or customary practice in the art. It is intended that the specification and examples be considered as exemplary only, with a true scope and spirit of the present disclosure being indicated by the following claims.

In the present disclosure, the terms "installed," "connected," "coupled," "fixed" and the like shall be understood broadly, and can be either a fixed connection or a detachable connection, or integrated, unless otherwise explicitly defined. These terms can refer to mechanical or electrical connections, or both. Such connections can be direct connections or indirect connections through an intermediate medium. These terms can also refer to the internal connections or the interactions between elements. The specific meanings of the above terms in the present disclosure can be understood by those of ordinary skill in the art on a case-by-case basis.

In the description of the present disclosure, the terms "one embodiment," "some embodiments," "example," "specific example," or "some examples," and the like can indicate a specific feature described in connection with the embodiment or example, a structure, a material or feature included in at least one embodiment or example. In the present disclosure, the schematic representation of the above terms is not necessarily directed to the same embodiment or example.

Moreover, the particular features, structures, materials, or characteristics described can be combined in a suitable manner in any one or more embodiments or examples. In addition, various embodiments or examples described in the specification, as well as features of various embodiments or examples, can be combined and reorganized.

In some embodiments, the control and/or interface software or app can be provided in a form of a non-transitory computer-readable storage medium having instructions stored thereon is further provided. For example, the non-transitory computer-readable storage medium can be a ROM, a CD-ROM, a magnetic tape, a floppy disk, optical data storage equipment, a flash drive such as a USB drive or an SD card, and the like.

Implementations of the subject matter and the operations described in this disclosure can be implemented in digital electronic circuitry, or in computer software, firmware, or hardware, including the structures disclosed herein and their structural equivalents, or in combinations of one or more of them. Implementations of the subject matter described in this disclosure can be implemented as one or more computer programs, i.e., one or more portions of computer program instructions, encoded on one or more computer storage medium for execution by, or to control the operation of, data processing apparatus.

Alternatively, or in addition, the program instructions can be encoded on an artificially-generated propagated signal, e.g., a machine-generated electrical, optical, or electromagnetic signal, which is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them.

Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, drives, or other storage devices). Accordingly, the computer storage medium can be tangible.

The operations described in this disclosure can be implemented as operations performed by a data processing apparatus on data stored on one or more computer-readable storage devices or received from other sources.

The devices in this disclosure can include special purpose logic circuitry, e.g., an FPGA (field-programmable gate array), or an ASIC (application-specific integrated circuit). The device can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The devices and execution environment can realize various different computing model infrastructures, such as web services, distributed computing, and grid computing infrastructures.

A computer program (also known as a program, software, software application, app, script, or code) can be written in any form of programming language, including compiled or interpreted languages, declarative or procedural languages, and it can be deployed in any form, including as a stand-alone program or as a portion, component, subroutine, object, or other portion suitable for use in a computing environment. A computer program can, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more portions, sub-programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform actions by operating on input data and generating output. The processes and logic flows can also be performed by, and apparatus can also be implemented as, special purpose logic circuitry, e.g., an FPGA, or an ASIC.

Processors or processing circuits suitable for the execution of a computer program include, by way of example, both general and special purpose microprocessors, and any one or more processors of any kind of digital computer. Generally, a processor will receive instructions and data from a read-only memory, or a random-access memory, or both. Elements of a computer can include a processor configured to perform actions in accordance with instructions and one or more memory devices for storing instructions and data.

Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented with a computer and/or a display device, e.g., a VR/AR device, a head-mount display (HMD) device, a head-up display (HUD) device, smart eyewear (e.g., glasses), a CRT (cathode-ray tube), LCD (liquid-crystal display), OLED (organic light emitting diode), or any other monitor for displaying information to the user and a keyboard, a pointing device, e.g., a mouse, trackball, etc., or a touch screen, touch pad, etc., by which the user can provide input to the computer.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components.

The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

While this specification contains many specific implementation details, these should not be construed as limitations on the scope of any claims, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination.

Moreover, although features can be described above as acting in certain combinations and even initially claimed as such, one or more features from a claimed combination can in some cases be excised from the combination, and the claimed combination can be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products.

As such, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking or parallel processing can be utilized.

It is intended that the specification and embodiments be considered as examples only. Other embodiments of the disclosure will be apparent to those skilled in the art in view of the specification and drawings of the present disclosure. That is, although specific embodiments have been described above in detail, the description is merely for purposes of illustration. It should be appreciated, therefore, that many aspects described above are not intended as required or essential elements unless explicitly stated otherwise.

Various modifications of, and equivalent acts corresponding to, the disclosed aspects of the example embodiments, in addition to those described above, can be made by a person of ordinary skill in the art, having the benefit of the present disclosure, without departing from the spirit and scope of the disclosure defined in the following claims, the scope of which is to be accorded the broadest interpretation so as to encompass such modifications and equivalent structures.

It should be understood that "a plurality" or "multiple" as referred to herein means two or more. "And/or," describing the association relationship of the associated objects, indicates that there may be three relationships, for example, A and/or B may indicate that there are three cases where A exists separately, A and B exist at the same time, and B exists separately. The character "/" generally indicates that the contextual objects are in an "or" relationship.

In the present disclosure, it is to be understood that the terms "lower," "upper," "under" or "beneath" or "underneath," "above," "front," "back," "left," "right," "top," "bottom," "inner," "outer," "horizontal," "vertical," and other orientation or positional relationships are based on example orientations illustrated in the drawings, and are merely for the convenience of the description of some embodiments, rather than indicating or implying the device or component being constructed and operated in a particular orientation. Therefore, these terms are not to be construed as limiting the scope of the present disclosure.

Moreover, the terms "first" and "second" are used for descriptive purposes only and are not to be construed as indicating or implying a relative importance or implicitly indicating the number of technical features indicated. Thus, elements referred to as "first" and "second" may include one or more of the features either explicitly or implicitly.

In the present disclosure, a first element being "on" a second element may indicate direct contact between the first and second elements, without contact, or indirect geometrical relationship through one or more intermediate media or layers, unless otherwise explicitly stated and defined. Similarly, a first element being "under," "underneath" or "beneath" a second element may indicate direct contact between the first and second elements, without contact, or indirect geometrical relationship through one or more intermediate media or layers, unless otherwise explicitly stated and defined.

Some other embodiments of the present disclosure can be available to those skilled in the art upon consideration of the specification and practice of the various embodiments disclosed herein. The present application is intended to cover any variations, uses, or adaptations of the present disclosure following general principles of the present disclosure and include the common general knowledge or conventional technical means in the art without departing from the present disclosure. The specification and examples can be shown as illustrative only, and the true scope and spirit of the disclosure are indicated by the following claims.

The invention claimed is:

1. A method of removing mites, applicable to a crawling mite remover, the method comprising:
   upon receiving a mite removing instruction, acquiring a target path for mite removal and switching from a hibernation state to a crawling state;
   in the crawling state, crawling according to the target path and performing mite removal during a crawling process; and
   switching from the crawling state to the hibernation state after crawling to an end position of the target path; and
   wherein
   the mite remover comprises a processor, a body, a first motor and a plurality of legs,
   the plurality of legs are disposed at a side of the body;
   the processor and the first motor are disposed in the body, the processor is connected to the first motor, and the first motor is connected to the plurality of legs;
   the processor is configured to send a movement signal to the first motor;
   based on the movement signal, the first motor drives the plurality of legs to perform a telescopic movement, driving the body to move on a surface of an object, and the body performs mite removal on the surface of the object;
   a dust box is provided at a top of the body, an upper shell is provided on an outer side of the dust box to protect the dust box, the body is provided with a bearing and a second motor, and the upper shell is connected to the body through the bearing;
   the processor is configured to send a steering signal to the second motor; and
   based on the steering signal, the second motor drives the bearing to rotate, and the second motor drives drive the body to rotate relative to the upper shell and to steer on the surface of the object.

2. The method according to claim 1, further comprising:
   determining a current position of the apparatus as an original position upon receiving the mite removing instruction; and
   in the crawling state, crawling according to the target path and performing mite removal during the crawling process comprise:
   crawling from the original position to a start position of the target path based on the crawling state; and
   crawling according to the target path from the start position and performing mite removal during the crawling process.

3. The method according to claim 2, wherein the switching from the crawling state to the hibernation state after crawling to the end position of the target path comprises:
   when crawling to the end position of the target path, continuing crawling to the original position; and
   when crawling to the original position, switching from the crawling state to the hibernation state.

4. The method according to claim 2, further comprising:
   determining a time when crawling to the start position of the target path as a start time of mite removal;
   determining a time when crawling to the end position of the target path as an end time of mite removal; and
   generating a mite removing log, the mite removing log comprising the start time of mite removal and the end time of mite removal; or the mite removing log comprising the start time of mite removal and a mite removing duration, the mite removing duration being determined by the start time of mite removal and the end time of mite removal.

5. The method according to claim 4, further comprising:
   sending the mite removing log to a connected terminal, and displaying the mite removing log by the terminal.

6. The method according to claim 1, wherein the acquiring a target path for mite removal and switching from a hibernation state to a crawling state upon receiving a mite removing instruction comprise:
   when receiving the mite removing instruction and determining that no moving object exists within a preset range, acquiring the target path and switching from the hibernation state to the crawling state.

7. A mite remover, comprising a processor, a body, a first motor, and a plurality of legs, wherein
   the plurality of legs are disposed at a side of the body;
   the processor and the first motor are disposed in the body, the processor is connected to the first motor, and the first motor is connected to the plurality of legs;
   the processor is configured to send a movement signal to the first motor; and
   based on the movement signal, the first motor drives the plurality of legs to perform a telescopic movement, driving the body to move on a surface of an object, and the body performs mite removal on the surface of the object; and
   wherein
   a dust box is provided at a top of the body, an upper shell is provided on an outer side of the dust box to protect the dust box, the body is provided with a bearing and a second motor, and the upper shell is connected to the body through the bearing;
   the processor is configured to send a steering signal to the second motor; and
   based on the steering signal, the second motor drives the bearing to rotate, and the second motor drives drive the body to rotate relative to the upper shell and to steer on the surface of the object.

8. The mite remover according to claim 7, wherein a dust suction port is provided at a bottom of the body;
   a passage is provided inside the body, and a turbine is provided in the passage;
   an interior of the dust box, the passage and the dust suction port are in communication; and
   the turbine is configured to rotate to suck dust on the surface of the object into the dust box through the passage from the dust suction port.

9. The mite remover according to claim 7, wherein an ultraviolet lamp is provided at a bottom of the body; and
   the ultraviolet lamp is configured to irradiate the surface of the object, and ultraviolet rays emitted by the ultraviolet lamp performs mite removal.

10. The mite remover according to claim 7, wherein the body is provided with a sensor, and the sensor is connected to the processor; and
    the sensor is configured to detect a position of the mite remover relative to the object, and when it is determined that the mite remover is located at an edge of the object, the processor sends the steering signal.

11. The mite remover according to claim 7, further comprising a communication module, wherein
the communication module is connected to the processor;
the communication module is configured to receive a target path sent by a terminal, and send the target path to the processor;
the body further comprises a positioning member, and the positioning member is connected to the processor;
the positioning member is configured to detect a current position of the mite remover and sends the current position to the processor; and
the processor is configured to control the first motor according to a positional relationship between the current position and the target path.

12. The mite remover according to claim 7, wherein each of the plurality of leg comprises a connector and a lower shell, the first motor is connected to the connector, and the connector is connected to the lower shell; and
the first motor is configured to drive the connector to perform a telescopic movement, the connector is configured to drive the lower shell to move on the surface of the object, and the body is configured to perform mite removal on the surface of the object.

13. The mite remover according to claim 12, wherein an upper shell is provided on an outer side of the dust box, the upper shell is hemispherical, and the lower shells of the plurality of legs are arc-shaped; and
the first motor is configured to drive the connectors of the plurality of legs to telescope and drive the lower shells of the plurality of legs to fit on a side of the body and contact the upper shell, and the upper shell and the lower shells of the plurality of legs constitute a sphere.

14. The mite remover according to claim 12, wherein the connector comprises a first joint and a second joint;
the first motor is connected to the first joint, the first joint is connected to the second joint, and the second joint is connected to the lower shell;
a third motor is provided between the first joint and the second joint;
the processor is configured send the movement signal to the third motor; and
based on the movement signal, the third motor is configured to drive the second joint to rotate relative to the first joint.

15. A method of removing mites, applicable to a mite remover, wherein the mite remover comprises a processor, a body, a first motor, and a plurality of legs; the plurality of legs is provided on a side of the body; the processor and the first motor are disposed inside the body, the processor is connected to the first motor, and the first motor is connected to the plurality of legs; and the method comprises:
the processor sending a movement signal to the first motor upon receiving a mite removing instruction; and
based on the movement signal, the first motor driving the plurality of legs to perform a telescopic movement and drive the body to move on a surface of an object, and the body performing mite removal on the surface of the object; and
wherein
a dust box is provided at a top of the body, an upper shell is provided on an outer side of the dust box to protect the dust box, the body is provided with a bearing and a second motor, and the upper shell is connected to the body through the bearing;
the processor is configured to send a steering signal to the second motor; and
based on the steering signal, the second motor drives the bearing to rotate, and the second motor drives drive the body to rotate relative to the upper shell and to steer on the surface of the object.

16. The method according to claim 15, wherein a dust suction port is provided at a bottom of the body; a passage is provided inside the body, and a turbine is provided in the passage; an interior of the dust box, the passage and the dust suction port are in communication; and the body performing mite removal on the surface of the object comprises:
the turbine rotating to suck dust on the surface of the object into the dust box through the passage from the dust suction port.

17. The method according to claim 15, wherein the mite remover further comprises a detection component, the detection component is connected to the processor, and the method further comprises:
the processor controlling the detection component to detect whether a moving object exists within a preset range of the mite remover; and
upon the processor receiving the mite removing instruction and determining that no moving object exists within the preset range, the processor sending the movement signal to the first motor.

18. The method according to claim 15, wherein the body further comprises a positioning component, and the positioning component is connected to the processor; and the method further comprises:
the positioning component detecting a first position of the mite remover and sending the first position to the processor, wherein the first position is a current position of the mite remover; and
the processor controlling the first motor according to a positional relationship between the first position and the target path.

19. The method according to claim 1, wherein
the mite removing instruction is an automated instruction based on timing;
the mite remover is configured to automatically start mite removal without user operation;
the end position of the target path is also an original position of the mite remover; and
the mite remover is further configured to generate a mite removing log for user viewing.

* * * * *